United States Patent
Dieterich et al.

(10) Patent No.: US 6,984,762 B2
(45) Date of Patent: Jan. 10, 2006

(54) PROCESS FOR THE TWO-STEP PRODUCTION OF DINITROTOLUENE

(75) Inventors: Erwin Dieterich, Köln (DE); Anke Hielscher, Leverkusen (DE); Berthold Keggenhoff, Krefeld (DE); Manfred Keller-Killewald, Brunsbüttel (DE); Jürgen Münnig, Kaarst (DE); Dietmar Wastian, Dormagen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 4 days.

(21) Appl. No.: 10/780,266

(22) Filed: Feb. 17, 2004

(65) Prior Publication Data

US 2004/0267061 A1    Dec. 30, 2004

(30) Foreign Application Priority Data

Feb. 20, 2003    (DE)    ................................. 103 07 140

(51) Int. Cl.
*C07C 205/00*    (2006.01)
(52) U.S. Cl. ....................................... 568/934; 568/932
(58) Field of Classification Search ................ 568/934, 568/932
See application file for complete search history.

(56) References Cited

U.S. PATENT DOCUMENTS 5,345,012 A    9/1994 Schieb et al. ............... 568/934
5,679,873 A *  10/1997 Klingler et al. ............. 568/934
6,258,986 B1    7/2001 Klingler et al. ............. 568/934

FOREIGN PATENT DOCUMENTS

EP    903 336 A2    3/1999

* cited by examiner

*Primary Examiner*—J. Parsa
(74) *Attorney, Agent, or Firm*—Joseph C. Gil; N. Denise Brown

(57) ABSTRACT

The invention relates to a process for the production of dinitrotoluene by the two-stage nitration of toluene. In the first stage of this process, toluene was reacted adiabatically with nitrating acid so that at least 90% of the toluene was reacted off and no more than 70% of the toluene formed dinitrotoluene. The resulting organic phase containing mononitrotoluene and the aqueous acid phase containing sulfuric acid were separated, and the aqueous acid phase containing sulfuric acid was concentrated by flash evaporation. The resulting concentrated sulfuric acid was recycled into the reaction in the first stage, and/or into the reaction in the second stage, and/or into the concentration in the second stage.
In the second stage, the organic phase containing mononitrotoluene from the first stage was completely reacted isothermally with nitrating acid. The organic phase and the aqueous acid phase containing sulfuric acid were then separated, and the aqueous acid phase containing sulfuric acid was concentrated by vacuum evaporation. The resulting concentrated sulfuric acid was recycled into the reaction in the first stage and/or the second stage.

7 Claims, 3 Drawing Sheets

PROCESS FOR THE TWO-STEP PRODUCTION OF DINITROTOLUENE

BACKGROUND OF THE INVENTION

The invention relates to a process for the nitration of toluene with nitrating acid to form dinitrotoluene (DNT) in a two-stage process, wherein the first stage is performed adiabatically and the second stage isothermally.

Dinitrotoluene (DNT) is the precursor of toluene diisocyanate, which is used as a raw material for the production of polyurethanes. The conventional industrial process for the production of dinitrotoluene is the isothermal two-stage reaction of toluene with nitrating acid, a mixture of nitric acid and sulfuric acid Ullmanns Encyklopädie der technischen Chemie, 4$^{th}$ edition, volume 17, page 392, Verlag Chemie, Weinheim 1979. In this process, a mixture of isomers of mononitrotoluene (MNT) is first produced, and is converted to dinitrotoluenes in a second, separate process step. However, the process has the disadvantage that the acid phase forming in both steps (substantially sulfuric acid) has to be freed of the water taken up, with high energy costs.

It is also known to convert toluene to dinitrotoluene in one step by an adiabatic route (EP-A-597 361). In this process, toluene is reacted with at least 2 equivalents of a nitrating acid of a specific composition by an adiabatic route, a final temperature of more than 120° C. being reached. After separating the phases at this temperature, the acid phase is fed into a concentrating stage (flash evaporation in vacuo), the heat content of the acid being utilised for the concentration. The concentrated acid is topped up with nitric acid and recycled into the process.

In this process, however, the difficulty arises that, during the flash evaporation, a certain portion of DNT dissolved in the acid passes into the gas phase together with the water distilling off and then solidifies during the condensation of the vapours under the condensation conditions of the water (melting point of the mixture of isomers 52–58° C.) and coats the heat exchanger. In addition, in the course of the process, temperatures are reached at which the DNT is not permanently stable in the presence of by-products. To guarantee the safety of the process, the permitted residence time of substance streams containing a high proportion of DNT at high temperatures must not be exceeded. This requires considerable expenditure on safety devices.

Various solutions have been proposed to the problem of interference with condensation caused by DNT contained in the vapours, such as alternately operated, staggered heat exchangers, contact condensers or injection condensers (R. A. Vauck, H. A. Müller, Grundoperationen chemischer Verfahrenstechnik, 5$^{th}$ edition, VEB Leipzig 1962, p. 447). In addition, EP-A-0696569 describes a process for the adiabatic production of DNT, wherein at least 5% MNT is deliberately retained in the reaction product of the adiabatic nitration to prevent the coating of the heat exchangers.

All these processes are costly from either a technical or an energy point of view, or they do not allow DNT to be produced with a very small proportion of MNT. Furthermore, the problem remains of the high temperature stress to which DNT or media containing high proportions of DNT are subjected.

The object of the present invention was therefore to provide a technically simple process for the production of dinitrotoluene by the nitration of toluene, in which at least part of the heat of reaction formed can be utilised for concentrating the waste acid and, at the same time, DNT and media containing DNT are not subjected to temperatures that are questionable from a safety point of view.

SUMMARY OF THE INVENTION

The invention relates to a process for the production of dinitrotoluene by the two-stage nitration of toluene. This process comprises a) in a first stage,
  (i) adiabatically reacting toluene with nitrating acid wherein at least 90%, preferably at least 98%, of the toluene is reacted off and no more than 70%, preferably no more than 50% of the toluene used reacts to form dinitrotoluene,
  (ii) separating the organic phase containing mononitrotoluene and the aqueous acid phase containing sulfuric acid,
  (iii) concentrating by flash evaporation the aqueous acid phase containing sulfuric acid, and
  (iv) recycling the resultant concentrated sulfuric acid into the reaction in the first step and/or into the reaction in the second step and/or into the concentration in the second stage, and b) in a second stage,
  (i) completely reacting isothermally the organic phase containing mononitrotoluene from the first step with nitrating acid,
  (ii) separating the organic phase and the aqueous acid phase containing sulfuric acid,
  (iii) concentrating the aqueous acid phase containing sulfuric acid by vacuum evaporation and
  (iv) recycling the resultant concentrated sulfuric acid into the reaction in the first stage and/or the second stage.

DETAILED DESCRIPTION OF THE INVENTION

Figure 1:
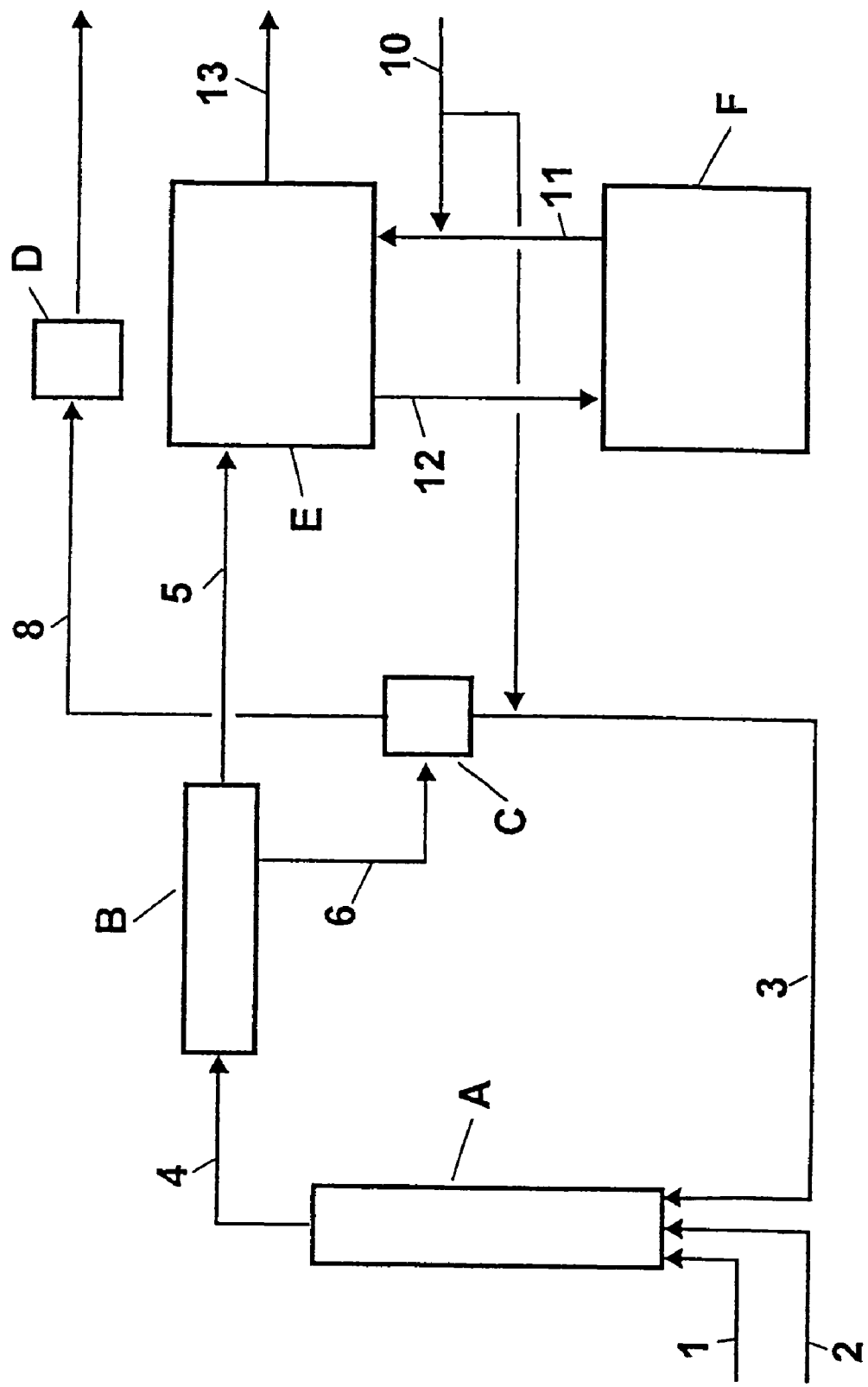
FIG. 1 is a schematic diagram of the process. In this embodiment, the organic phase and the aqueous acid phase from the first step are initially separated, and then the aqueous acid phase is concentrated by flash evaporation.

In the process according to the invention, preferably 98% of the toluene is allowed to react off in the first stage, and up to 50%, more preferably up to 30% of the toluene used is preferably being converted to dinitrotoluene.

The first, adiabatic stage of the process can be carried out in any suitable reactor. However, tubular reactors are preferably used, the length of which can be from 2 to 20 m and the diameter from 25 to 2000 mm. The length and the diameter are preferably selected such that the average residence time is 10 to 300 seconds. Tubular reactors without, or preferably tubular reactors with, suitable inserts for dispersing the two-phase mixture can be used. Inserts that can be used advantageously include, for example, sieve trays or static mixing elements, such as are described in, for example, e.g. in U.S. Pat. No. 5,616,818 (believed to correspond to EP-A-0708076) and U.S. Pat. No. 4,994,242 (believed to correspond to EP-A-0489211), the disclosures of which are herein incorporated by reference.

The nitrating acid used preferably contains from 80 to 100 percent by weight (wt. %) inorganic components, which are substantially composed of 50 to 90 wt. % sulfuric acid, 1 to 20 wt. % nitric acid and at least 5 wt. % water, based on the total wt. of inorganic components. The balance of the nitrating acid is constituted by organic compounds such as MNT and DNT. The molar ratio of nitric acid:toluene is preferably at least 0.7:1 and no more than 1.8:1, more preferably no more than 1.5:1.

The nitric acid used can have a concentration of 50 to 100 wt. %. Preferably, 62–70 wt. % nitric acid is used.

The nitrating acid is mixed with toluene at the reactor entrance, which can take place using a simple line feed or special mixing elements such as jets or special static mixers. The toluene is preferably dispersed in the nitrating acid by means of a dispersing element such as, e.g., a jet disperser.

On entering the reactor, the mixture is preferably at a temperature of 80 to 120° C., and rises to 120 to 170° C. by the time it leaves the reactor owing to the heat of reaction. The temperature increase is preferably 20 to 80° C.

After leaving the reactor, the two-phase mixture is separated into the aqueous acid phase which contains sulfuric acid, and the organic phase containing mononitrotoluene. This separation preferably takes place in one or more static phase separators.

The organic phase can then be used, in its entirety or in part, to extract the waste acid from the second step. It can then be fed into the second nitrating stage. The organic phase preferably contains no more than 10 wt. %, more preferably less than 2 wt. % toluene, and preferably no more than 70 wt. %, more preferably less than 50 wt. % and most preferably up to 30 wt. % DNT, based on the total weight of organic phase.

The aqueous acid phase (waste acid) is freed of the water, preferably from 60 to 110% of the water, formed during the reaction and that fed in with the nitric acid by flash evaporation, preferably under a pressure of 10 to 400 mbar, optionally with additional heat input via suitable heat exchangers, is then fed back to the reactor entrance. The precise amount of water formed during the reaction and fed in with the nitric acid is preferably evaporated. However, deviations from this preferred state of equilibrium can be compensated for by exchanging quantities of sulfuric acid from the circulation in the first stage with waste acid from the circulation in the second stage and/or with concentrated sulfuric acid from the acid concentration in the second stage.

In another embodiment of the process, the flash evaporation and phase separation steps are carried out in reverse order. In other words, the two-phase mixture is subjected to the flash evaporation under the above conditions, after which the cooled mixture is separated into the acid phase and the organic phase.

The organic components which are carried over into the vapors owing to the volatility of the water vapor are condensed together with the water. Because of the high proportion of MNT, there is no risk of solid deposits of DNT or DNT/MNT forming in the vapor condenser. The two-phase vapor condensate is separated into the organic phase and the aqueous phase, which can preferably take place in one or more static separators. The organic phase can be used, in its entirety or in part, to extract the waste acid in the second stage, and can then be fed into the second nitrating stage.

The second, isothermal stage of the process is carried out in a suitable reactor or a series of reactors with a cooling device. Stirred tank reactors or loop reactors with heat exchangers, as described in Ullmanns Encyklopädie der technischen Chemie, $4^{th}$ edition, volume 17, page 392, Verlag Chemie, Weinheim 1979, are preferably used. The reaction temperature in this case is conventionally adjusted by means of heat dissipation with cooling water and is preferably 60 to 95° C., more preferably 60 to 80° C. The residence time is preferably 1 to 10 min.

The organic phase from the first stage of the process, which contains mononitrotoluene (MNT) and may have been used beforehand, in its entirety or in part, to extract the aqueous acid phase of the second stage, is fed into the reactor or reactor cascade and mixed with nitrating acid. The nitrating acid is preferably produced by mixing concentrated sulfuric acid at a concentration of 83 to 98 wt. %, more preferably 85 to 98 wt. % and nitric acid. The quantity of nitrating acid used in the second nitrating step is selected such that the sum of the nitric acid used in the first and in the second nitrating steps is from 1.9 to 2.2 moles, preferably from 2.0 to 2.05 moles per mole of toluene used. The concentration of the nitric acid used is preferably the same as that used in the first nitrating step.

The two-phase mixture formed by the reaction in the second stage is separated into the organic phase and the aqueous acid phase containing sulfuric acid, which can take place by means of centrifuges or, preferably, in one or more static separators. The organic phase is freed of traces of acid by suitable means such as, e.g. by extraction with water and/or soda solution, and thus the end product, dinitrotoluene, is obtained.

The acid phase obtained (waste acid) is preferably first extracted with MNT-containing organic phase from the first stage to reduce the content of dissolved DNT. All or part of the organic vapor condensate from the first stage and/or all or part of the organic phase from the first stage can be utilised for this purpose. This can take place in one or more steps, and mixer-separator units or agitated extractor columns can be used. Before or after the extraction, some of the waste acid can be diverted and added to the sulfuric acid in the first nitrating stage before or after the concentration.

After the extraction, the waste acid from the dinitration is freed of the water formed during the reaction and that is fed in with the nitric acid in suitable distillation apparatus. A suitable distillation method is described e.g. in U.S. Pat. No. 6,156,288 (believed to correspond to DE-A-19636191), the disclosure of which is herein incorporated by reference. The waste acid flowing into the distillation apparatus preferably has a concentration of 75 to 90 wt. % sulfuric acid, and is preferably concentrated to a concentration of 83 to 98 wt. %, more preferably 85 to 98 wt. % sulfuric acid.

Optionally, to equalise the sulfuric acid balance in the first stage, up to 30% of the waste acid forming in the adiabatically operated part (the first stage), preferably sulfuric acid after the flash evaporation, can be fed into this acid concentration stage. To equalise the sulfuric acid balance in the isothermally operated stage, a corresponding quantity of the sulfuric acid leaving the acid concentration stage must then be added to the acid circulation in the first stage.

Sulfuric acid losses from both reaction stages can be replaced with commercially available 80 to 100 wt. %, preferably 90 to 100 wt. % sulfuric acid.

The process according to the invention is explained in more detail below with reference to the figures.

DETAILED DESCRIPTION OF THE FIGURES

An embodiment of the process according to the invention is illustrated diagrammatically in FIG. 1. In FIG. 1, A denotes the reactor in the first stage, B the phase separator of the reaction mixture, C the flash evaporator (flash evaporator with a heat exchanger in the bottom) of the aqueous acid phase in the first stage, D the condenser of the flash evaporator, E the reactor and the phase separator in the second stage and F the vacuum evaporator for concentrating the aqueous acid phase from the second stage. In this embodiment of the process, toluene (stream 1), nitric acid (stream 2) and recycled, concentrated sulfuric acid (stream 3) are fed into reactor A and mixed. The two-phase reaction mixture obtained (stream 4) is then separated in the phase separator B into an organic phase (stream 5) and an aqueous acid phase (stream 6). The aqueous acid phase (stream 6) is concentrated in the flash evaporator C. The vapors (stream 8) formed in the flash evaporator C are condensed in the condenser D and can be discharged from the process. The concentrated aqueous acid phase (which is substantially sulfuric acid) (stream 3) is fed back to the reactor A in the first stage. The organic phase (stream 5) is introduced into the reactor E in the second stage and reacts there with nitrating acid to form dinitrotoluene. The separation of the organic phase, which contains dinitrotoluene, and the aqueous acid phase is not illustrated in FIG. 1 as a step in itself. The organic phase is discharged as stream 13 and processed further. The aqueous acid phase 12 (waste acid) is transferred into the vacuum evaporator F in the second stage, where the concentration of the waste acid takes place. The concentrated, aqueous acid phase is then recycled as stream 11 back to the entrance to the reactor E. To compensate for losses of sulfuric acid, fresh sulfuric acid (stream 10) is added. The addition takes place into the streams of concentrated sulfuric acid 3 and 11.

Figure 2:
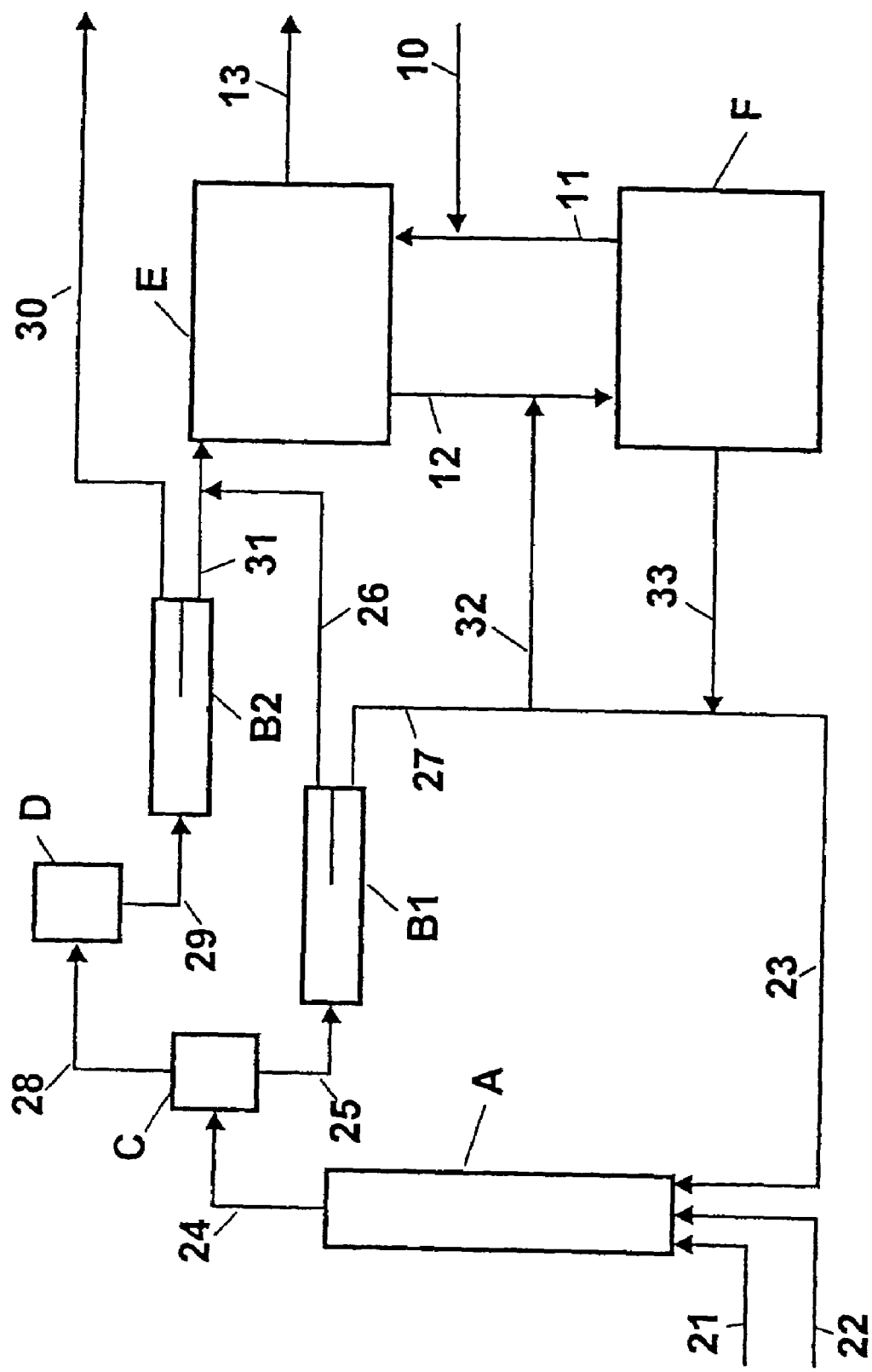
FIG. 2 is another schematic diagram of the process. In this embodiment, the organic phase and the aqueous acid phase initially undergo the flash evaporation together and then the organic phase and the concentrated aqueous acid phase are separated.

FIG. 2 shows an alternative embodiment of the process according to the invention. Toluene (stream 21), nitric acid (stream 22) and concentrated sulfuric acid (stream 23) are reacted in the first stage in reactor A to form a mixture of mononitrotoluene and dinitrotoluene. The two-phase reaction mixture obtained (stream 24) is then passed into the flash evaporator C. The vapors obtained there (stream 28) are condensed in the condenser D and the condensate (stream 29) is fed into the phase separator B2 and separated there into an organic phase (stream 31) and an aqueous phase (stream 30). The aqueous phase (stream 30) is discharged from the process. The liquid phase obtained in the flash evaporator C (concentrated sulfuric acid and organic phase) (stream 25) is separated in the phase separator B1 into an organic phase (stream 26) and an aqueous acid phase (stream 27). A part of the concentrated sulfuric acid (stream 32) is transferred together with stream 12 into the vacuum evaporator F in the second stage. The remaining quantity of stream 27 is brought together with concentrated sulfuric acid (stream 33) from the second stage and returned to the reactor A in the first stage as stream 23. The organic phases from the phase separators B1 (stream 26) and B2 (stream 31) are combined and fed into the reactor E in the second stage. There, the organic phases containing mononitrotoluene (stream 26+31) are reacted with nitrating acid there to form dinitrotoluene. The separation of the organic phase containing dinitrotoluene and the aqueous acid phase is not shown in FIG. 2 as a step in itself. The organic phase is discharged as stream 13 and processed further. The aqueous acid phase 12 is transferred into the vacuum evaporator F in the second stage, where the concentration of the waste acid takes place. The concentrated sulfuric acid is then recycled back to the entrance of reactor E as stream 11. To compensate for losses of sulfuric acid, fresh sulfuric acid (stream 10) is added. This addition takes place into the acid stream 11.

Figure 3:
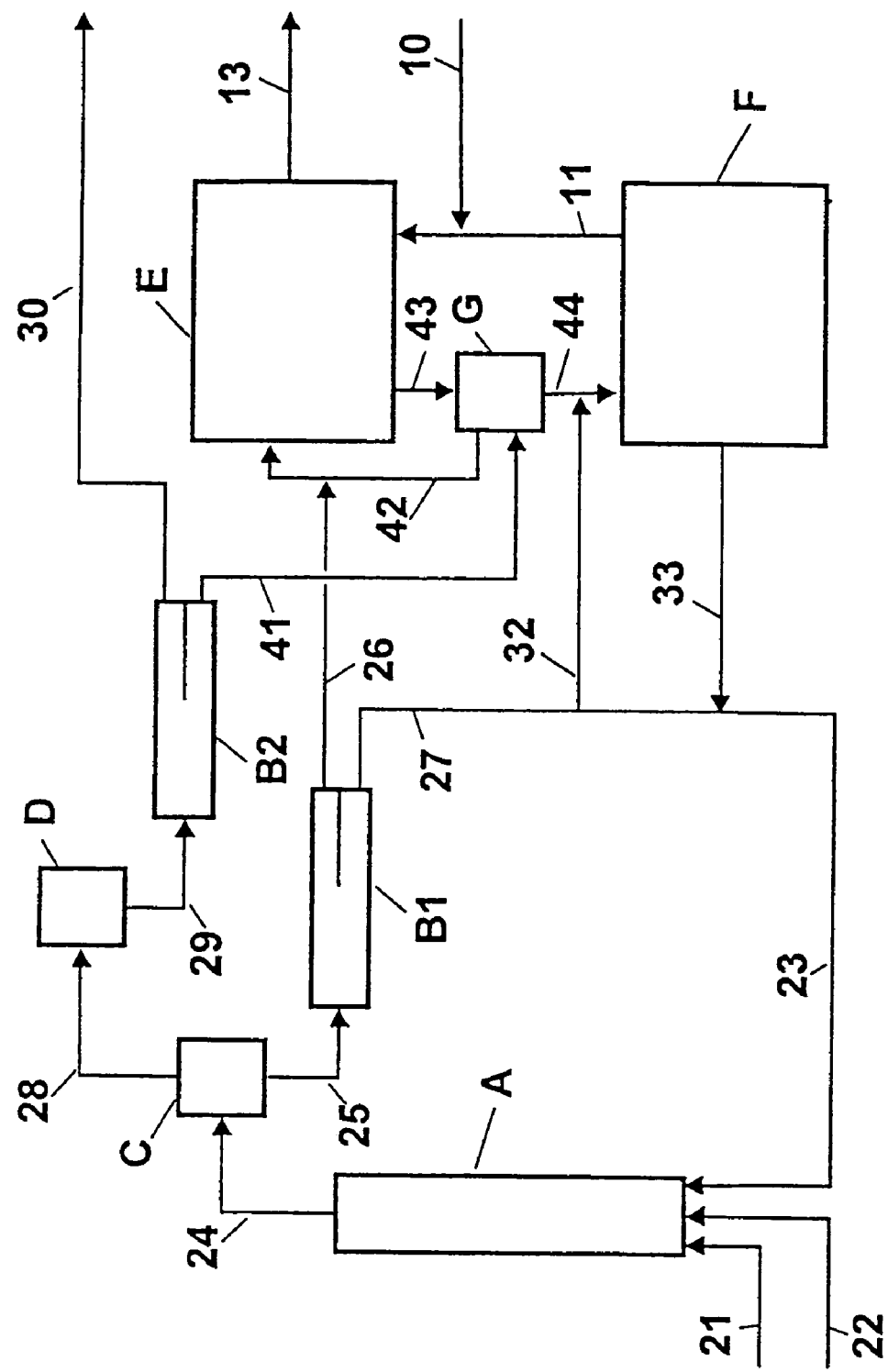
FIG. 3 is another schematic diagram of the process. In this embodiment, the organic phase and the aqueous acid phase initially undergo the flash evaporation together and then the organic phase and the concentrated aqueous acid phase are separated; and the aqueous acid phase from the second stage is extracted with the organic vapor condensate from the first stage.

FIG. 3 shows a particular embodiment of the process variant shown in FIG. 2, which is supplemented by an extraction step. In the extraction apparatus G, the aqueous acid phase (stream 43) from the second stage is extracted with the organic vapor condensate (stream 41) from the first stage. The DNT content of the aqueous acid phase (stream 44) is thereby reduced. The organic phase from the phase separator B1 (stream 26) and that from the extractor G (stream 42) are combined and fed into the reactor E in the second stage. Otherwise, the labels in FIG. 3 have the same meanings as in FIG. 2.

EXAMPLES

Example 1

An apparatus according to FIG. 1 was used. The temperatures and compositions of the substance streams are compiled in Table 1.

In the first stage, operated adiabatically, 50.6 kg/h of toluene (stream 1), 63.0 kg/h of 68 percent by weight (wt. %) nitric acid (stream 2) and 1066.6 kg/h of 76.8 wt. % concentrated waste acid (stream 3) were mixed intensively at the entrance to reactor A. The dimensions for reactor A were as follows: length (L)=5 m, and diameter (D)=25/80 mm). In the tubular reactor fitted with perforated discs for redispersion, the temperature rose to 131° C. With an average residence time of 15 min, the reaction mixture (stream 4) was separated in the phase separator B into 78.1 kg/h of an organic phase (stream 5) and 1102.1 kg/h of an aqueous acid phase (stream 6). The 74.5 wt. % waste acid was concentrated to a sulfuric acid content of 76.8 wt. % in the flash evaporator C operated at 40 mbar. For this purpose, slight secondary heating was provided in the bottom of the flash evaporator by means of a heat exchanger. The concentrated waste acid (stream 3) was fed into the reaction again.

The vapors separated off in the flash evaporator C (35.7 kg/h, stream 8) were then condensed in the heat exchanger D. Owing to the high MNT content of 78 wt. %, based on the organic proportion in the vapor stream, no deposits formed in the vapor condenser D.

The organics separated off in the phase separator (78.1 kg/h, stream 5) was fed into the second stage (reactor E). 96.0 kg/h of DNT (stream 13) were produced there by the addition of nitrating acid in a loop reactor E cooled to approx. 70° C. The waste acid forming there was freed of excess water in the vacuum evaporator (or acid concentrator) F.

By performing the reaction adiabatically, it was possible to utilise the heat of reaction in the first step for concentrating the waste acid. In comparison to a mononitration performed isothermally, this resulted in a savings of heating steam of approx. 40% for the process overall. Safety investigations of the reaction mixture (stream 4) at the adiabatic reaction final temperature of 131° C. gave no indications whatsoever of incipient decomposition. Even with a stress period of more than 90 minutes, no exothermic reactions appeared that were questionable from a safety point of view.

Example 2

An apparatus according to FIG. 2 was used. The temperatures and compositions of the substance streams are compiled in Table 2.

In the first stage, operated adiabatically, 50.6 kg/h of toluene (stream 21), 62.9 kg/h of 68 wt. % nitric acid (stream 22) and 736.0 kg/h of 78.6 wt. % concentrated waste acid (stream 23) were mixed intensively at the entrance to reactor A. The dimensions for reactor A were as follows: L=8 m, D=80 mm. In the tubular reactor fitted with perforated discs for redispersion, the temperature rose to 138° C. The reaction mixture (stream 24) was depressurised via a nozzle into the flash evaporator C operated at 40 mbar, where part of the water and organic components evaporated. The vapors were then condensed in the heat exchanger D. Despite cooling with cold water at 18° C., no deposits formed in the vapor condenser D. The vapor condensate (stream 29) was separated in phase separator B2 into an aqueous phase (21.3 kg/h, stream 30) and an organic phase (57.6 kg/h, stream 31). The organic phase, consisting predominantly of MNT, was fed into the second stage (reactor E).

The acid/DNT/MNT mixture (stream 25) after being cooled to 94° C. by flash evaporation, was freed of undissolved DNT/MNT in phase separator B1. The separated mixture (20.2 kg/h, stream 26) was fed into the dinitration together with stream 31. A partial stream (83.8 kg/h, stream 32) of the waste acid concentrated to 77.1 wt. % (750.4 kg/h, stream 27) was fed into the vacuum evaporator (or acid concentrator) F in the second step, where it was concentrated to 93 wt. %, and then returned into the acid circulation in the first stage (stream 33).

In the dinitration E, 96.1 kg/h of DNT (stream 13) were produced in a loop reactor cooled to approx. 70° C. from the two feeds 31 and 26 by the addition of nitrating acid. The waste acid forming there was freed of excess water in the vacuum evaporator (or acid concentrator) F.

By performing the reaction adiabatically in the first stage, it was possible to separate off a considerable part of the water introduced by the process without bringing in any outside energy.

Example 3

An apparatus according to FIG. 3 was used. The temperatures and compositions of the substance streams are compiled in Table 3.

In the first stage, operated adiabatically, 50.6 kg/h of toluene (stream 21), 63.0 kg/h of 68 wt. % nitric acid (stream 22) and 1306.6 kg/h of 82.4 wt. % concentrated waste acid (stream 23) were mixed intensively at the entrance to reactor A. The dimensions of reactor A were as follows: L=5 m, D=80 mm. In the tubular reactor fitted with perforated discs for redispersion, the temperature rose to 132° C. The reaction mixture (stream 24) was depressurised via a nozzle into the flash evaporator C operated at 40 mbar, where part of the water and organic components evaporated. The vapors were then condensed in the heat exchanger D. Despite cooling with cold water at 18° C., no deposits formed in the vapor condenser D. The vapor condensate (stream 29) was separated in phase separator B2 into the aqueous phase (18.3 kg/h, stream 30) and organic phase (56.4 kg/h, stream 41).

The acid/DNT/MNT mixture (stream 25) after being cooled to 109° C. by flash evaporation, was freed of undissolved DNT/MNT in phase separator B1. The separated mixture (21.4 kg/h, stream 26) was fed into the second stage (reactor E). A partial stream (137.5 kg/h, stream 32) of the waste acid concentrated to 81.3 wt. % (1324.1 kg/h, stream 27) was fed into the vacuum evaporator (or acid concentrator) F in the second stage, where it was concentrated to 93 wt. %, and then returned into the acid circulation in the first stage (stream 33).

In the second stage 96.2 kg/h of DNT (stream 13) were produced in a loop reactor E cooled to approx. 70° C. from the two feeds 42 and 26 by the addition of nitrating acid. Part of the dissolved DNT was removed from the waste acid forming there (stream 43) in the extraction apparatus G with organic vapor condensate from the first step (stream 41). The waste acid (stream 44) from the extraction was then freed of excess water in the vacuum evaporator (or acid concentrator) F. The organic phase from the extraction apparatus G (59.4 kg/h, stream 42) was fed into the dinitration reactor E together with stream 26.

By performing the reaction adiabatically in the first stage, it was possible to separate off a considerable part of the water introduced without bringing in any outside energy.

The temperatures and compositions of the streams described in Examples 1–3 are listed in Tables 1–3, respectively.

TABLE 1

| | | Substance stream no. | | | | | | | |
|---|---|---|---|---|---|---|---|---|---|
| | | 1 | 2 | 3 | 4 | 5 | 6 | 8 | 13 |
| Temperature | ° C. | 20.0 | 20.0 | 100.0 | 131.3 | 131.3 | 131.3 | 100.0 | 68.0 |
| Total stream | kg/h | 50.59 | 62.98 | 1066.60 | 1180.17 | 78.10 | 1102.08 | 35.68 | 101.55 |
| Toluene | kg/h | 50.59 | | | | | | | |
| MNT | kg/h | | | 0.12 | 57.73 | 55.13 | 2.60 | 2.48 | |
| DNT | kg/h | | | 1.81 | 25.29 | 22.76 | 2.53 | 0.72 | 95.98 |
| H2SO4 | kg/h | | | 817.25 | 817.25 | 0.16 | 817.08 | | 1.11 |
| HNO3 | kg/h | | 42.83 | 0.01 | 0.12 | | 0.12 | 0.11 | |
| H2O | kg/h | | 20.15 | 247.42 | 279.79 | 0.04 | 279.74 | 32.37 | 0.44 |

TABLE 2

| | | Substance stream no. | | | | | | |
|---|---|---|---|---|---|---|---|---|
| | | 13 | 21 | 22 | 23 | 24 | 25 | 26 |
| Temperature | °C. | 68.0 | 20.0 | 20.0 | 94.2 | 138.3 | 94.4 | 94.4 |
| Total stream | kg/h | 101.01 | 50.59 | 62.94 | 735.96 | 849.48 | 770.64 | 20.21 |
| Toluene | kg/h | | 50.59 | | | | | |
| MNT | kg/h | | | | 0.13 | 57.74 | 3.19 | 3.05 |
| DNT | kg/h | 96.12 | | | 1.70 | 25.18 | 19.07 | 17.17 |
| H2SO4 | kg/h | 0.66 | | | 577.22 | 577.22 | 577.21 | |
| HNO3 | kg/h | | | 42.80 | 0.01 | 0.08 | 0.01 | |
| H2O | kg/h | 0.34 | | 20.14 | 156.90 | 189.26 | 171.16 | |

| | | Substance stream no. | | | | | |
|---|---|---|---|---|---|---|---|
| | | 27 | 29 | 30 | 31 | 32 | 33 |
| Temperature | °C. | 94.4 | 27.3 | 27.3 | 27.3 | 94.4 | 40.0 |
| Total stream | kg/h | 750.43 | 78.84 | 21.25 | 57.59 | 83.80 | 68.51 |
| Toluene | kg/h | | | | | | |
| MNT | kg/h | 0.14 | 54.55 | 2.46 | 52.09 | 0.02 | |
| DNT | kg/h | 1.91 | 6.11 | 0.61 | 5.50 | 0.21 | 0.00 |
| H2SO4 | kg/h | 577.21 | | | | 64.46 | 63.67 |
| HNO3 | kg/h | 0.01 | 0.08 | 0.08 | | | |
| H2O | kg/h | 171.16 | 18.11 | 18.11 | | 19.11 | 4.83 |

TABLE 3

| | | Substance stream no. | | | | | | | |
|---|---|---|---|---|---|---|---|---|---|
| | | 13 | 21 | 22 | 23 | 24 | 25 | 26 | 27 |
| Temperature | °C. | 68.0 | 20.0 | 20.0 | 104.3 | 132.3 | 109.4 | 109.4 | 109.4 |
| Total stream | kg/h | 101.01 | 50.59 | 63.01 | 1306.59 | 1420.19 | 1345.50 | 21.44 | 1324.07 |
| Toluene | kg/h | | 50.59 | | | | | | |
| MNT | kg/h | | | | 0.18 | 57.79 | 4.53 | 4.32 | 0.21 |
| DNT | kg/h | 96.19 | | | 1.71 | 25.21 | 19.02 | 17.11 | 1.90 |
| H2SO4 | kg/h | 0.66 | | | 1074.44 | 1074.44 | 1074.43 | | 1074.43 |
| HNO3 | kg/h | | | 42.85 | 0.02 | 0.14 | 0.02 | | 0.02 |
| H2O | kg/h | 0.34 | | 20.16 | 230.24 | 262.62 | 247.51 | | 247.51 |

| | | Substance stream no. | | | | | | | |
|---|---|---|---|---|---|---|---|---|---|
| | | 29 | 30 | 32 | 33 | 41 | 42 | 43 | 44 |
| Temperature | °C. | 27.3 | 27.3 | 109.4 | 40.0 | 27.3 | 54.4 | 68.0 | 54.4 |
| Total stream | kg/h | 74.69 | 18.26 | 137.47 | 119.01 | 56.43 | 59.40 | 235.97 | 233.00 |
| Toluene | kg/h | | | | | | | | |
| MNT | kg/h | 53.26 | 2.40 | 0.02 | | 50.86 | 42.72 | | 8.14 |
| DNT | kg/h | 6.19 | 0.62 | 0.20 | 0.00 | 5.57 | 16.68 | 14.29 | 3.18 |
| H2SO4 | kg/h | 0.01 | 0.01 | 111.55 | 110.61 | | | 187.70 | 187.70 |
| HNO3 | kg/h | 0.12 | 0.12 | | | | | 0.01 | 0.01 |
| H2O | kg/h | 15.11 | 15.11 | 25.70 | 8.39 | | | 33.97 | 33.97 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of dinitrotoluene by the two-stage nitration of toluene, comprising
   a) in a first stage,
      (i) reacting toluene adiabatically with nitrating acid, wherein at least 90% of the toluene is reacted off and no more than 70% of the toluene used reacts to form dinitrotoluene,
      (ii) separating the organic phase containing mononitrotoluene and the aqueous acid phase containing sulfuric acid,
      (iii) concentrating the aqueous acid phase containing sulfuric acid by flash evaporation and
      (iv) recycling the resultant concentrated sulfuric acid into the reaction in the first stage, the reaction in the second stage, the vacuum evaporator in the second stage, or a combination thereof; and
   b) in a second stage,
      (i) completely reacting isothermally the organic phase containing mononitrotoluene from the first stage with nitrating acid,
      (ii) separating the organic phase and the aqueous acid phase containing sulfuric acid,
      (iii) concentrating the aqueous acid phase containing sulfuric acid by vacuum evaporation, and
      (iv) recycling the resultant concentrated sulfuric acid into the reaction in the first stage, the reaction in the second stage, or a combination thereof.

2. The process of claim 1, wherein in a)(i) the adiabatic reaction of toluene with nitrating acid, at least 98% of the toluene is reacted off and up to 50% of the toluene used reacts to form dinitrotoluene.

3. The process of claim 1, wherein the organic phase from a)(ii) contains no more than 10 wt. % of toluene and no more than 70 wt. % of dinitrotoluene.

4. A process for the production of dinitrotoluene by the two-stage nitration of toluene comprising:
  a) in a first stage,
    (i) reacting toluene adiabatically with nitrating acid, wherein at least 90% of the toluene is reacted off and no more than 70% of the toluene used reacts to form dinitrotoluene,
    (ii) jointly concentrating the organic phase containing mononitrotoluene and the aqueous acid phase containing sulfuric acid from the first stage by flash evaporation,
    (iii) separating the organic phase containing mononitrotoluene and the aqueous acid phase containing sulfuric acid, and
    (iv) recycling the resultant concentrated sulfuric acid into the reaction in the first stage, the reaction in the second stage, the vacuum evaporator in the second stage, or a combination thereof, and
  b) in a second stage,
    (i) completely reacting isothermally the organic phase containing mononitrotoluene from the first stage with nitrating acid,
    (ii) separating the organic phase and the aqueous phase containing sulfuric acid,
    (iii) concentrating the aqueous acid phase containing sulfuric acid by vacuum evaporation, and
    (iv) recycling the resultant concentrated sulfuric acid into the reaction in the first stage, the reaction in the second stage, or a combination thereof.

5. The process of claim 4, wherein in a)(i) the adiabatic reaction of toluene with nitrating acid, at least 98% of the toluene is reacted off and up to 50% of the toluene used reacts to form dinitrotoluene.

6. The process of claim 4, wherein the organic phase from a)(ii) contains no more than 10 wt. % of toluene and no more than 70 wt. % of dinitrotoluene.

7. The process of claim 4, wherein the aqueous acid phase containing sulfuric acid from the second stage is extracted with an organic phase containing mononitrotoluene from the first stage before the vacuum evaporation.

* * * * *